United States Patent [19]

Neiditch et al.

[11] Patent Number: 5,023,329

[45] Date of Patent: Jun. 11, 1991

[54] SUCROSE-6-ESTER PRODUCTION PROCESS

[75] Inventors: David S. Neiditch; Nicholas M. Vernon; Robert E. Wingard, Jr., all of Athens, Ga.

[73] Assignee: Noramco, Inc., Athens, Ga.

[21] Appl. No.: 512,692

[22] Filed: Apr. 23, 1990

[51] Int. Cl.$^5$ ............... C07H 13/00; C07H 23/00; C07H 1/00; C08B 37/00
[52] U.S. Cl. .................... 536/119; 536/115; 536/116; 536/120; 536/121; 536/124
[58] Field of Search ............... 536/119, 115, 116, 120, 536/122, 124, 18.6, 4.1, 121

[56] References Cited

U.S. PATENT DOCUMENTS

| 4,343,934 | 8/1982 | Jenner et al. | 536/122 |
| 4,362,869 | 12/1982 | Jenner et al. | 536/122 |
| 4,380,476 | 4/1983 | Mufti et al. | 536/119 |
| 4,435,440 | 3/1984 | Hough et al. | 536/4.1 |
| 4,950,746 | 8/1990 | Navia | 536/119 |

OTHER PUBLICATIONS

David et al., "Regioselective Manipulation of Hydroxyl Groups Via Orbanotin Derivatives", Tetrahedron, vol. 41, No. 4, pp. 643–663 (1985).

Wagner et al., "Preparation and Synthetic Utility of Some Organotin Derivatives of Nucleosides", Wagner et al., J. Org. Chem., vol. 39, No. 1, pp. 24–30 (1974).

Holzapfel et al., "Sucrose Derivatives and the Selective Benzoylation of the Secondary Hydroxyl Groups of 6,1',6'-tri-O-tritylsucrose", S. Afr. Tydskr. Chem., 1984, 37(3), pp. 57–61.

Primary Examiner—Ronald W. Griffin
Assistant Examiner—Everett White
Attorney, Agent, or Firm—Charles J. Metz

[57] ABSTRACT

Process which comprises reacting sucrose with a di-(hydrocarbyl)tin oxide in an inert organic reaction vehicle with removal of water for a period of time and at a temperature sufficient to produce a 1,3-di-(6-O-sucrose)-1,1,3,3-tetra(hydrocarbyl)distannoxane.

15 Claims, No Drawings

SUCROSE-6-ESTER PRODUCTION PROCESS

This invention relates to a process for producing sucrose derivatives, which process comprises reacting sucrose directly with a di(hydrocarbyl)tin oxide to produce a 6-O-sucrose distannoxane compound useful as an intermediate in the production of, inter alia, the artificial sweetener, sucralose.

BACKGROUND OF THE INVENTION

The sucrose molecule contains three primary hydroxyl groups and five secondary hydroxyl groups. Therefore, when it is desired to prepare derivatives of sucrose involving reaction of the hydroxyl groups, it can be a major synthesis problem to direct the reaction only to the desired hydroxyl groups. For instance, the artificial sweetener 4,1',6'-trichloro-4,1',6'-trideoxygalactosucrose ("sucralose") is derived from sucrose by replacing the hydroxyls in the 4, 1, and 6' positions with chlorine. (In the process of making the sweetener, the stereo configuration at the 4 position is reversed—hence the compound is a galactosucrose.) This compound and methods for synthesizing it are disclosed in U. S. Pat. Nos. 4,343,934, 4,362,869, 4,380,476, and 4,435,440. The direction of the chlorine atoms to only the desired positions is a major synthesis problem, especially since the hydroxyls that are replaced are of differing reactivity (two are primary and one is secondary; the synthesis is further complicated by the fact that the primary hydroxyl in the 6 position is unsubstituted in the final product). The preparation of this sweetener is only one illustration of the synthesis of sucrose derivatives wherein it is desired either to derivatize certain specific hydroxyl groups, and only such hydroxyl groups, or to derivatize only a specified number of the hydroxyls, perhaps in this latter case without particular regard to which particular hydroxyl(s) are derivatized. The preparation of sucrose-based mono-ester surfactants is a commercial example of mono substitution on the sucrose molecule.

This invention provides an improved and more efficient means for synthesizing sucrose compounds such as 6-substituted sucrose derivatives wherein the process of the invention is highly regioselective both with regard to directing the reaction strictly to the 6 position and to the preparation of mono-substituted derivatives only. The term "regioselective" refers to a reaction that highly favors a single major product. (Ref., Hassner, "Regiospecificity. A Useful Terminology in Addition and Elimination Reactions", J. Org. Chem., 33, No. 7, 2684–6, July 1968.)

The distannoxane-based preparation of sucrose-6-esters was first described in Navia, PROCESS FOR SYNTHESIZING SUCROSE DERIVATIVES BY REGIOSELECTIVE REACTION, U.S. patent application Ser. No. 220,641, filed on July 18, 1988 (now U.S. Pat. No. 4,950,746), and assigned to the same assignee as this application. Navia disclosed that a suitable di(hydrocarbyl)tin-based species, such as dibutyltin oxide, dioctyltin oxide, dibutyltin dimethoxide, or the like, can be combined with a hydroxyl group-containing compound such as a monohydric alcohol or a simple phenol in such a way as to produce a reactive distannoxane intermediate [i.e., a 1,3-di(hydrocarbyloxy)-1,1,3,3-tetra(hydrocarbyl)distannoxane], which can then be reacted with sucrose to afford a 1,3-di-(6-O-sucrose)-1,1,3,3-tetra(hydrocarbyl)distannoxane. Navia also described the ready preparation of sucrose-6-esters by the treatment of these organotin-sucrose adducts with a suitable acylating agent in an appropriate solvent or solvent mixture. Navia further described the simple esters acetate and benzoate, prepared from their anhydrides, as preferred protecting groups for sucralose manufacture because of cost, toxicological considerations, and ease of subsequent removal. The process disclosed by Navia for the distannoxane-mediated preparation of sucrose 6-esters ("S-6-E") thus consists of three distinct steps, as follows (using dibutyltin oxide and n-butanol as exemplary reactants):

(1) Reaction of dibutyltin oxide ("DBTO") with a large stoichiometric excess of n-butanol, with azeotropic removal of water, to produce 1,3-dibutoxy-1,1,3,3-tetrabutyldistannoxane ("DBDS"), which has been shown to exist as a monohydrate;

(2) Reaction of DBDS with sucrose in N,N-dimethylformamide ("DMF") with removal of water and n-butanol to form 1,3-di-(6-O-sucrose)-1,1,3,3-tetrabutyldistannoxane, more commonly referred to as dibutylstannoxylsucrose ("DBSS"). Because the acylation reaction of the next step should be done in a hydroxyl-free environment for optimum yield of the sucrose ester product, all the n-butanol and water must be removed during this step and replaced with DMF; and (3) Reaction of DBSS with a slight stoichiometric excess of an acylating agent such as acetic anhydride to form a sucrose-6-acylate such as sucrose-6-acetate ("S-6-A").

By following this reaction sequence, S-6-A is typically produced in good yields, with only minimal contamination by residual sucrose, sucrose diacetates, and other sucrose monoacetates.

As will be appreciated by those skilled in the art of industrial chemistry, the above-described three-step sequence suffers several drawbacks with regard to economical commercial implementation. These drawbacks become especially serious if commercial implementation using batch-mode processing is desired. The first drawback is the solvent exchange of DMF for n-butanol during DBSS formation. Because of the temperature sensitivity of DBSS in this solvent matrix (decomposition appears to begin at about 90° C.), this solvent exchange must be accomplished as part of a vacuum distillation requiring ever increasing vacuum as the n-butanol content of the mixture declines. Failure to remove sufficient n-butanol results in poor performance in the acetylation reaction of Step (3). Additionally, recycle of the distilled n-butanol is made complex because of its contamination by DMF and water. (Recycling of the n-butanol is required for economic reasons.)

A second drawback of the three-step process is the moisture sensitivity of DBDS (and related condensation products of tin oxides with alcohols or phenols). Even though DBDS apparently exists as a monohydrate, contact with atmospheric moisture results in its rapid reversion to DBTO and n-butanol. DBDS must therefore be handled under conditions designed to rigorously exclude atmospheric moisture. In a manufacturing operation, conditions which resulted in the deposition of DBTO onto the surfaces of the processing equipment would necessitate an expensive clean-up operation because DBTO is a polymeric solid that is quite insoluble in most solvents.

A third drawback involves the recycle of the organotin end-product, distannoxane diacetate ("DSDA"). DSDA is reconverted to DBDS by extraction followed by treatment with either potassium or sodium butoxide. The by-products of these conversions, either potassium or sodium acetate, are difficult to filter. This difficult filtration causes the loss of DBDS, and would be expected to have an adverse impact on S-6-A production cost. Also, as pointed out above, the DBDS must be protected from moisture.

The process of this invention avoids these three problems, and in addition provides a simpler, more economically attractive and less trouble-prone process for the manufacture of sucrose-6-esters. This process is especially suitable for use in the batch-processing mode. We have discovered that sucrose may be directly reacted with di(hydrocarbyl)tin oxides, such as DBTO, in a polar aprotic solvent, such as DMF, in the presence of a cosolvent capable of both promoting the dissolution of DBTO and effecting the codistillative removal of all water generated in the reaction of the tin oxide with sucrose, to produce thereby an organotin-sucrose adduct. This adduct has been shown by NMR to be a distannoxane of a structure identical to that produced by the alcohol-mediated method of Navia (e.g., DBSS). As was the case with the Navia process, the DBSS can be readily acylated in situ to afford good yields of S-6-E.

The process of this invention is an improvement over the alcohol-mediated process of Navia for the following reasons:

(a) one reactant (i.e., an alcohol such as butanol) has been eliminated;

(b) a moisture-sensitive intermediate (e.g., DBDS) has been eliminated;

(c) a complex vacuum distillation-solvent exchange has been eliminated, along with the need to recover n-butanol (or a similar hydroxylic reactant) from mixtures containing DMF and water;

(d) a simplified organotin recycle process, involving an easily filterable di(hydrocarbyl)tin oxide (such as DBTO) rather than a difficultly filterable acetate salt and a moisture-sensitive organotin derivative, is now possible [this recycle process is described in copending United States Patent Application Serial No. (NOR 9), PROCESS FOR RECOVERY OF ORGANOTIN ESTERS FROM REACTION MIXTURES CONTAINING THE SAME AND RE-USE OF THE RECOVERED ORGANOTIN COMPOUNDS, filed on the same day as this application by N. M. Vernon and R. E. Walkup (Vernon et al.), and assigned to the same assignee as this application]; and (e) sucrose-6-esters, such as S-6-A or sucrose-6-benzoate ("S-6-B"), are obtained in a better yield and in a higher state of purity (apparently the result of eliminating one transition state from the process pathway).

BRIEF SUMMARY OF THE INVENTION

The invention provides a process which comprises reacting sucrose with a di(hydrocarbyl)tin oxide in an inert organic vehicle for a period of time and at a temperature sufficient to produce a 1,3-di-(6-O-sucrose)-1,1,3,3-tetra(hydrocarbyl)distannoxane. In a preferred aspect of the invention, this 1,3-di-(6-O-sucrose)-1,1,3,3-tetra-(hydrocarbyl)distannoxane is then reacted with an acylating agent at a temperature and for a period of time sufficient to produce a sucrose-6-ester.

THE PRIOR ART

In a review article entitled REGIOSELECTIVE MANIPULATION OF HYDROXYL GROUPS VIA ORGANOTIN DERIVATIVES, Tetrahedron, Vol. 41, No. 4, pp 643-663 (1985), David et al. disclose the reaction of tin compounds with hydroxyl-group containing compounds to produce stannoxyl compounds, which can then be alkylated or acylated to produce ethers or esters. The reaction of bis(tributyltin) oxide with various carbohydrates (including sucrose), followed by acylation to produce a mixture of esters of varying degrees of substitution, is disclosed. The use of dibutyltin oxide in a reaction with carbohydrates is also disclosed in the article. The authors report the preparation of two dialkylstannylene carbohydrate derivatives, the 2,3-O-dibutylstannylene derivative of methyl 4,6-O-benzylidene-α-D-glucopyranoside and 4,6-O-benzylidene-2,3-dibutylstannylene-α-D-mannopyranoside. The proposed molecular structures of these two stannylene derivatives are shown in FIGS. 3 and 4 on page 645 of the article.

Wagner et al., J. Org. Chem., 39, 24 (1974), disclose the preparation of dibutylstannylene derivatives of nucleosides by reacting dibutyltin oxide with nucleosides in refluxing methanol. After stripping off the methanol, the stannylene derivative was acylated by reaction with equimolar quantities of acid chloride and triethylamine.

Holzapfel et al., in "Sucrose Derivatives and the Selective Benzoylation of the Secondary Hydroxyl groups of 6,1',6'-tri-O-tritylsucrose", S. Afr. Tydskr. Chem, 1984,37(3), pages 57-61, disclose the reaction of dibutyltin oxide with 6,1',6'-tri-O-tritylsucrose, followed by reaction with benzoyl chloride to produce a 72% yield of 3'-O-benzoyl-6,1',6'-tri-O-tritylsucrose and 9% of the 2-O-benzoate derivative, and minor amounts of the 2,3'-dibenzoate derivative.

The basic teachings of the prior art (as represented by the above-cited authors) is that the reactivity of a hydroxyl group is increased by the formation of a bond with tin, but in polyhydroxylated compounds such as sugars it cannot be predicted a priori which hydroxyl group will be activated (see pages 646-7 of the cited David et al. paper, in the section entitled "Stereoelectronic consequences of the Sn-O bond.—nucleophilic enhancement of the oxygen atom", particularly the last paragraph of this section).

The fact that sucrose will react directly with a di(hydrocarbyl)tin oxide to produce a high yield of a discreet distannoxane derivative capable of further chemical utilization is novel, and could not have been predicted by those skilled in the art. (The terminology "will react directly" means that sucrose reacts with the tin oxide without the use of any intermediate reactants or reactions, such as first reacting the tin oxide with an alcohol or phenol, as is done in the Navia process, described above. This direct reaction of sucrose with the tin oxide is an important feature of this invention.) Even more surprising is that the discreet chemical entity has a structure in which the oxygen atom of the sucrose-6-hydroxyl is covalently bonded to tin, and is therefore nucleophilically enhanced. Those skilled in the art would have predicted a structure containing only a single tin atom, such as a stannylene, to be a much more likely reaction product.[1] (A stannylene may be defined as a carbohydrate derivative possessing an intramolecular C-O-Sn-O-C bonding sequence.) Such a species would probably not be capable of being cleanly converted to a sucrose-6-ester. All previously described conversions involving the direct reaction of carbohydrates with di(hydrocarbyl)tin oxides are reported to afford stannylene products, with those products possessing five-membered rings being preferred. Stannylene formation has been reported to be the case for 6,1',6'-tri-O-tritylsucrose[2], various disaccharides[3], nucleosides[4], and an extremely wide variety of miscellaneous monosaccharides[5]. The stannylene structure of several of these materials has been confirmed by x-ray crystallography[6] and NMR spectroscopy[7].

There is no precedent for the direct reaction of a carbohydrate with a di(hydrocarbyl)tin oxide to produce a 1,3-carbohydrate-substituted distannoxane. This unexpected result may be unique to the sucrose molecule.

REFERENCES AND FOOTNOTES

1) For a good review of the structure of products arising from the reactions of di(hydrocarbyl)tin oxides with carbohydrates, consult: S. David and S. Hanessian, Tetrahedron, 41, 643 (1985).

2) C. Holzapfel et al., S. Afr. J. Chem., 37, 57 (1984).

3) J. Alais et al., Tetrahedron Lett., 2883 (1983).

4) D. Wagner et al., J. Org. Chem., 39, 24 (1974); M. Ikehara et al., Tetrahedron, 31, 1369 (1975); H. Takaku et al., Bull. Chem. Soc. Jpn., 56, 1424 (1983); H. Takaku et al., J. Org. Chem., 49, 51 (1984).

5) M. Nashed et al., Tetrahedron Lett., 3503 (1976); R. Munavu et al., J. Org. Chem., 41, 1832 (1976); C. Auge et al., J. Chem. Soc. Chem. Commun., 375 (1976); T. Ogawa et al., Carbohydr. Res., 56, C1 (1977); M. Nashed et al., ibid., 56, 419 (1977); M. Nashed, ibid., 60, 200 (1978); S. Hanessian et al., J. Am. Chem. Soc., 101 3839 (1979); V. Srivastava et al., Tetrahedron Lett., 3269 (1979); C. Auge et al., J. Chem. Soc. Perkin Trans. I, 1825 (1979); S. David et al., ibid., 1796 (1981); Y. Tsuda et al., Chem. Pharm. Bull., 31, 1612 (1983); Y. Tsuda et al., ibid., 31, 3778 (1983); C. Holzapfel et al., S. Afr. J. Chem., 37, 19 (1984); M. Haque, et al., Chem. Pharm. Bull., 35, 1016 (1987).

6) S. David et al., Nouveau J. Chim., 3, 63 (1979); C. Holzapfel et al., S. Afr. J. Chem. 35, 80 (1982).

7) S. Blunden et al., Carbohydr. Res., 88, 9 (1981).

DETAILED DESCRIPTION OF THE INVENTION

The process of the invention is carried out by reacting sucrose with a di(hydrocarbyl)tin oxide (DHTO) in an inert organic vehicle. The DHTO's that can be used include di(hydrocarbyl)tin oxides in which the hydrocarbyl groups bonded to tin can be, individually, alkyl, cycloalkyl, aryl, or arylalkyl such as, for example, methyl, ethyl, propyl, butyl, octyl, benzyl, phenethyl, preferred hydrocarbyl groups are alkyl having up to eight carbon atoms. In place of the tin oxide, a di(hydrocarbyl)tin dialkoxide, dihalide, or diacylate can be used. Dibutyltin oxide and dioctyltin oxide are particularly preferred, and dibutyltin oxide is the most preferred organotin oxide for use in the invention.

The DHTO and sucrose may be employed in a wide range of stoichiometric ratios. However, stoichiometric ratios of about one-to-one are preferred. This is because the use of an excess of sucrose leads to contamination of the S-6-E by sucrose and undesired sucrose esters, while the use of excess DHTO causes contamination of the S-6-E product by sucrose diesters. The most preferred stoichiometric ratio uses the DHTO in a very slight (1-3%) molar excess (basis sucrose) in order to insure the near absence of sucrose in the product.

The process of the invention is carried out in an inert organic reaction vehicle. By "inert" is meant that the reaction vehicle is free of any organic functional groups that will react with either the sucrose or the DHTO. For instance, functional groups such as alcoholic or phenolic hydroxyl that will react with di(hydrocarbyl)-tin oxide to produce 1,3-di(hydrocarbyloxy)-1,1,3,3-tetra(hydrocarbyl)distannoxane according to the process of Navia are to be avoided. In many cases, in order to accomplish the objectives of the invention, the inert organic reaction vehicle will be a mixed solvent system comprising a polar aprotic solvent and a cosolvent. The polar aprotic solvent is employed for the purpose of dissolving the sucrose, and the cosolvent is employed for the purpose of codistillatively removing the water generated by the reaction of sucrose with the DHTO and also promoting the solubility of the DHTO.

Polar aprotic solvents which can be employed include DMF, dimethyl sulfoxide (DMSO), N-methylpyrrolidinone (NMP), N,N-dimethylacetamide (DMA), hexamethylphosphoramide (HMPA), and other polar, aprotic solvents in which sucrose is soluble. DMF is the preferred polar aprotic solvent because of its low cost, its relatively low boiling point, and its suitability as a solvent for further steps in the process for producing sucralose.

Cosolvents capable of codistillatively removing the water of condensation include chlorinated hydrocarbons such as chloroform, a variety of saturated and aromatic hydrocarbons such as hexane, heptane, octane, cyclohexane, benzene, and toluene, ketones such as methyl ethyl ketone and methyl isobutyl ketone, acyclic and cyclic ethers such as methyl tert-butyl ether and tetrahydrofuran, and other inert organic liquids that meet the criteria set forth herein. A very wide range of organic liquids are suitable for use as cosolvents in the invention. The primary criteria for a cosolvent are (1) that it produce a mixture with the polar aprotic solvent, the DHTO, and the sucrose, which refluxes at atmospheric pressure with an internal reaction temperature within the range of from about 75° C. to about 125° C., (2) that it codistill the water produced by the condensation of the DHTO and sucrose, thereby facilitating removal of water during the reaction, and (3) that it promote the solubility of the DHTO in the reaction mixture (since DHTO's are usually not soluble to any significant degree in polar aprotic solvents) and thereby enhance the rate of reaction of the DHTO with sucrose. By the term "promote the solubility of the DHTO" is meant that the cosolvent at least partially solubilize the DHTO under the conditions of the process of the invention.

The cosolvent does not have to be capable of forming a constant-boiling azeotrope of constant composition with water to be an effective cosolvent, nor is it necessary that the cosolvent be immiscible with water. It is necessary only that the cosolvent be capable of codistilling the water of condensation from the reaction medium.

Cosolvents which are immiscible with water and which do a constant-composition minimum-boiling azeotrope with water are preferred, but, as may be determined by an inspection of the Examples below, reaction systems employing such cosolvents typically reflux at temperatures significantly higher than either the water-azeotrope boiling point or the boiling point of the pure solvent. There are also data showing that the water-cosolvent compositions of the distillates arising from these systems are not constant throughout the DHTO-sucrose condensation period.

Preferred cosolvents for reasons of chemical stability, efficiency of water removal, cost, and boiling point include cyclohexane, n-heptane, and isooctane (2,2,4-trimethylpentane).

The reaction between sucrose and the DHTO is carried out at a temperature within the range of from about 75° C. to about 125° C. Below 75° C., the reaction becomes uneconomically slow, and above 125° C. there is a tendency for the carbohydrate to decompose. The preferred reaction temperature is within the range of about 80° C. to about 100° C., and more preferably, from about 85° C. to about 90° C.

Reaction temperatures are typically controlled in an empirical manner by adjusting the ratio of the polar aprotic solvent to the lower boiling cosolvent. Solvent to cosolvent ratios are not a narrowly critical aspect of the invention. For example, solvent to cosolvent ratios (vol/vol) of from about one-to-one to about ten-to-one are useful for the practice of this invention, with ratios of from about eight-to-five to eight-to-one having been demonstrated in the laboratory. Solvent to cosolvent ratios are limited by practical considerations. Too much cosolvent will inhibit sucrose solubility and could produce a mixture with a boiling point too low for a reasonable conversion time. Too little cosolvent can adversely effect the rate of di(hydrocarbyl)tin-sucrose adduct formation by reducing DHTO solubility and by limiting the rate at which water can be codistilled from the reaction mixture. Also, the use of too little cosolvent can result in reaction temperatures high enough to cause thermal degradation of the carbohydrate species.

A wide range of solids (DHTO and sucrose) to solvents (polar aprotic solvent and cosolvent) ratios are useful for the practice of the invention. This is not considered to be a narrowly critical aspect of the invention, provided that there is sufficient polar aprotic solvent present to insure the dissolution of the sucrose, and sufficient cosolvent present to insure water removal and to provide a desirable reaction temperature. Experimentally, solids-to-solvents ratios (wt/vol) of from about one-to-two to about one-to-six have been employed. The more concentrated systems are preferred for reasons of economics and practicality.

The reflux time required for the complete formation of the distannoxane-sucrose adduct is strictly a function of the efficiency of the removal of all the water of condensation (plus any water present from the use of wet reactants or solvents) from the system by codistillation. (Note that one equivalent of water is produced for each tin oxide equivalent.) The efficiency of water removal from the reaction system is a function of a number of interactive variables. These variables, which to a large extent can be experimentally controlled, include: (a) the internal reaction temperature; (b) the boiling point of the cosolvent; (c) the water content of the codistillate; (d) the rate of heat input to the system; (e) the efficiency of agitation; and (f) the reactor configuration employed.

Solid polymeric DBTO possesses water of hydration which amounts to one-half equivalent of water per equivalent of tin oxide. (This water of hydration was quantitated by several methods, the most useful of which were Karl Fischer water assays of DBTO dissolved in glacial acetic acid.) The condensation reaction between sucrose and DBTO releases this water of hydration. Thus, the water produced by the process of the invention for removal by codistillation is a sum of the water of condensation and the released water of hydration. The stoichiometry of the process is therefore one mole of water produced for codistillation per mole of tin oxide. Throughout this application the term "water of condensation" is employed to mean total water of reaction (i.e., the sum of both types water) as per the one mole-to-one mole stoichiometry.

Sucrose-organotin adduct formation times of from about two hours to about twenty-four hours have been employed experimentally. The reflux period is terminated when the theoretical amount of water has been codistilled from the system. This determination is usually made by a water analysis using the Karl Fischer method. Water removal usually accounts for from about 101% to 110% of theory. The excess water is the result of adventitious moisture present in the solvent, cosolvent, and sucrose. By appropriate manipulation of the variables described above, total required reflux times in the three to five hour range can typically be experimentally achieved.

After completion of the water removal, the normally biphasic (but solids-free) reaction mixtures are cooled to room temperature or below and acylated. Acid anhydrides are preferred acylating agents. The selection of the particular acylating agent to be used in the acylation reaction is dictated in part by the use to which the acylated product is to be put. For example, if the acyl group is being employed as a blocking group, as it would be in the preparation of the artificial sweetener as discussed above in the Background of the Invention section of this application, an acylating agent such as benzoic or acetic anhydride would be employed because it is inexpensive, the acyl group is readily removed at an appropriate stage of the synthesis, and it is stable to reactions that the acylated compound must undergo prior to removal of the acyl group. If a sucrose-6-ester is to be the ultimate product of the synthesis, then the acylating agent used is the one that will generate the desired acyl group for the ester product. With these principles in mind, among the acylating agents that can be used are the various anhydrides and acid halides of benzoic and substituted benzoic acid (e. g., 4-nitrobenzoic acid, 3,5-dinitro-benzoic acid, and the like), alkanoic acids such as acetic acid, propionic acid, butyric acid, cyclohexanecarboxylic acid, long chain fatty acids, both saturated and unsaturated, such as stearic acid, oleic acid, linoleic acid, and the like, having up to, for example, 28 carbon atoms, unsaturated acids such as acrylic acid and methacrylic acid, substituted acids such chloroacetic acid, cyanoacetic acid, phenoxyacetic acid, and the like, and saturated and unsaturated dicarboxylic acids such as phthalic acid, maleic acid, glutaric acid, and the like.

If the anhydride is a liquid, it may be added neat to the reaction mixture product of the sucrose/tin oxide condensation reaction, or it may be diluted with an inert cosolvent. If the anhydride is a solid, it may be added in the solid form or added as a solution in an appropriate inert solvent. The anhydride may be added all at once, or it may be added slowly over a period of time.

Anhydride stoichiometry is an important aspect of the successful practice of this invention. The use of too little anhydride will result in a S-6-E product contaminated by residual sucrose. The use of too much anhydride will cause sucrose diester contamination. The most preferred stoichiometric ratio uses the anhydride in a slight (5–10%) molar excess (basis sucrose) in order to insure the near absence of sucrose in the product.

Acylation temperatures from below 0° C. to about 30° C. have been employed experimentally. The upper limit of acceptable acylation temperatures is governed by the onset of thermally activated nonregioselective acylation reactions which will result in the formation of undesirable sucrose mono- and diesters. From a practical standpoint, this temperature limit is a function of the reactivity of the acid anhydride. For example, because acetic anhydride is a relatively reactive species, acylations with it are normally carried out below about 20° C. Benzoic anhydride, on the other hand, being somewhat less reactive, allows for acylation at room temperature or slightly above.

The acylation reactions are mildly exothermic. Depending upon initial reaction temperature and rate of anhydride addition to the di(hydrocarbyl)tin-sucrose adduct, external cooling of the acylation process might be required in order that thermally activated nonregioselective acylation be minimized.

The times required for the acylations of the sucrose adducts to go to completion are dependent upon the concentration of the reactants (as the acylation is a multiple-order process), the reactivity of the acylating agent, and the temperature of the reaction mixture. Although times of from one hour to several days have been employed in the laboratory, there is no advantage to extending the reaction period longer than that time necessary for consumption of the acylating agent. This is generally complete within from about one to about five hours under typical conditions.

When the sucrose-6-ester is to be employed in the production of sucralose, the post-acylation reaction mixtures contain S-6-E, polar aprotic solvent, cosolvent, and 1,3-di(hydrocarboxy)-1,1,3,3-tetra(hydrocarbyl)-distannoxane or distannoxane diester (DSDE), which is the tin-containing end-product of the sequence of reactions. The S-6-E products may be recovered from the mixtures by a variety of techniques. For example, the volatile solvents can be removed by evaporative and/or vacuum evaporative techniques to produce a syrup or gum consisting primarily of S-6-E and DSDE. The sucrose derivative can then be isolated by precipitation or crystallization from a solvent in which it is insoluble, but in which the DSDE is soluble. Alternatively, the relatively volatile cosolvent can be removed by evaporation and the DSDE extracted (for recycle) from the polar aprotic solvent by a suitable nonmiscible solvent, such as is disclosed in Vernon et al., cited above. Evaporation of the polar aprotic solvent will produce a syrup or gum consisting primarily of S-6-E and residual polar aprotic solvent. Solid S-6-E may be isolated by precipitation or crystallization techniques.

A preferred mode for the practice of this invention involves the production of the above-described DSDE-free syrup possessing about one or two parts DMF per part of S-6-E (w/w). This syrup is directly suitable for the preparation of sucralose-6-esters and sucralose by chlorination (such as the chlorination process described in copending United States patent application Ser. No. 382,147, IMPROVED SUCROSE-6-ESTER CHLORINATION, filed July 18, 1989, by R. E. Walkup, N. M. Vernon, and J. L. Navia, and assigned to the same assignee as this application).

The process of the invention affords S-6-E in yields from about the mid-70's to about the mid-90's. The unCrystallized produCts normally contain trace amounts of residual sucrose and somewhat larger amounts Of sucrose diesters. Sucrose monoesters having alternate attachment sites are typically not produced by this process. For example, normal S-6-E yields for the acetate and benzoate cases range between 86 and 94%. Sucrose diesters usually account for from about 3% to about 10% of the original sucrose, and from about 0.5% to about 1.5% of the original sucrose is recovered in unreacted form.

A detailed illustrative description of the process of the invention follows for a specific case involving DBTO as the di(hydrocarbyl)tin oxide, DMF as the polar aprotic solvent, n-heptane as the cosolvent, and benzoic anhydride as the acylating agent.

Sucrose (1.00 mol equiv) and DBTO (1.05 mol equiv) were suspended in DMF (about 6 ml per gram of sucrose) and n-heptane (about 3 ml per gram of sucrose), and the mixture was vigorously refluxed and stirred for three hours. The mixture was free of solids after about 30 minutes, and the reaction temperature was 98° C. The water removed from the reaction mixture by codistillation was trapped in a Dean-Stark water separator, and analyzed by the Karl Fischer method. It corresponded to 104% of theory (basis one water per tin oxide). The DBSS solution was cooled in an ice bath, treated dropwise with a solution of benzoic anhydride (1.10 mol equiv) in DMF, and then stirred several hours, first at ice-bath temperatures and then at room temperature. The crude product mixture, containing primarily sucrose-6-benzoate, distannoxane dibenzoate (DSDB), DMF, and n-heptane, was then treated with water and extracted with cyclohexane (about 15 ml per gram of sucrose) to remove DSDB according to the teachings of Vernon et al., cited above. The DMF solution was then subjected to rotary evaporation under high vacuum to remove entrained n-heptane, water, and a portion of the DMF to afford a syrup determined by HPLC to contain a 95.9% yield of S-6-B. HPLC analysis also showed the syrup to contain no detectable other sucrose monobenzoate species, a 3.57% yield of sucrose dibenzoates, and a 0.46% recovery of sucrose. The tin content of the syrup was found to be 0.1% by AA spectrophotometry. This syrup is suitable for chlorination to produce sucralose-6-benzoate.

The examples below illustrate the invention:

EXAMPLE 1

PREPARATION OF SUCROSE-6-BENZOATE USING DIOCTYLTIN OXIDE, DIMETHYLFORMAMIDE, AND HEPTANE

A 1000-ml, three-neck, round-bottom flask, equipped with mechanical stirrer, thermometer, and Dean-Stark water separator topped with a reflux condenser, was charged with 68.5 g (200 mmol) of sucrose, 75.8 g (210 mmol) of dioctyltin oxide, 400 ml of DMF, and 200 ml of n-heptane.

The suspension was heated to reflux (98° C. reaction temperature), and the resulting clear solution refluxed for 3 hr. The contents of the water separator were removed, dissolved in anhydrous isopropanol, and analyzed for water by the Karl Fischer method (4.03 g, 224 mmol, 107% of theory).

The solution was cooled to about 5° C., treated dropwise with 49.8 g (220 mmol) of benzoic anhydride dissolved in 50 ml of ice-cold DMF, and stirred for an additional 60 min at about 5° C. The formation of S-6-B ($R_f$ 0.5) and the disappearance of sucrose ($R_f$ 0.2) were followed by $SiO_2$ TLC (15:10:2, $CHCl_3$-$CH_3OH$-$H_2O$, sprayed with 5% ethanolic $H_2SO_4$ and charred).

After stirring overnight at room temperature under argon, the reaction mixture was treated with water (50 ml), extracted with cyclohexane (2×500 ml) to remove tin by-products, and the DMF evaporated (rotary evaporator, mechanical-pump vacuum, 30° C. water bath) to afford a light-brown viscous oil determined by HPLC analysis to contain 80.4 g (180 mmol, 90.1% yield) of sucrose-6-benzoate. The oil was shown by AA spectrophotometry to contain 0.1% tin.

EXAMPLE 2

PREPARATION OF SUCROSE-6-ACETATE USING DIOCTYLTIN OXIDE, DIMETHYLFORMAMIDE, AND ISOOCTANE

A 1000-ml, three-neck, round-bottom flask, equipped with mechanical stirrer, thermometer, and Dean-Stark water separator topped with a reflux condenser, was charged with 68.5 g (200 mmol) of sucrose, 75.8 g (210 mmol) of dioctyltin oxide, 400 ml of DMF, and 200 ml of isooctane (2,2,4-trimethylpentane). The suspension was heated to reflux (101° C. reaction temperature), and the resulting clear solution refluxed for 3 hr. The contents of the water separator were removed, dissolved in anhydrous isopropanol, and analyzed (Karl Fisher) for water (3.99 g, 222 mmol, 106% theory).

The solution was cooled to about 5° C., treated dropwise with 22.5 g (220 mmol) of acetic anhydride dissolved in 50 ml of ice-cold DMF, and stirred for an additional 3 hr at about 5° C. The formation of sucrose-6-acetate ($R_f$ 0.4) was followed using the TLC system described in Example 1.

After stirring overnight at room temperature under argon, the reaction mixture was treated with water (50 ml), extracted with cyclohexane (2×500 ml), and the DMF evaporated (rotary evaporator, mechanical-pump vacuum, 30° C. water bath) to afford a brownish viscous oil determined by HPLC analysis to contain 60.3 g (157 mmol, 78.5% yield) of sucrose-6-acetate. AA spectrophotometry gave a 0.2% tin content for this oil.

EXAMPLE 3

PREPARATION OF SUCROSE-6-BENZOATE USING DIBUTYLTIN OXIDE, DIMETHYLFORMAMIDE, AND CYCLOHEXANE

A 1000-ml, three-neck, round-bottom flask, equipped with mechanical stirrer, thermometer, and Dean-Stark water separator topped with a reflux condenser, was charged with 68.5 g (200 mmol) of sucrose, 52.3 g (210 mmol) of dibutyltin oxide, 400 ml of DMF, and 100 ml of cyclohexane. The suspension was heated to reflux (93° C. reaction temperature), and the resulting clear solution refluxed for 4 hr. The contents of the water separator were removed, dissolved in anhydrous isopropanol, and analyzed for water by the Karl Fisher method (3.97 g, 221 mmol, 105% of theory).

The solution was cooled to about 5° C., treated dropwise with 49.8 g (220 mmol) of benzoic anhydride dissolved in 50 ml of ice-cold DMF, and stirred an additional 30 min at about 5° C. After stirring overnight at room temperature under argon, the reaction mixture was treated with 50 ml of H₂O, extracted with 1000ml of cyclohexane, and the DMF evaporated (rotary evaporator, mechanical-pump vacuum, 30° C. water bath) to afford a light-tan viscous oil determined by HPLC analysis to contain 84.2 g (188 mmol, 94.4% yield) of sucrose-6-benzoate.

EXAMPLE 4

PREPARATION OF SUCROSE-6-ACETATE USING DIBUTYLTIN OXIDE, DIMETHYLFORMAMIDE, AND BENZENE

A 1000-ml, three-neck, round-bottom flask, equipped with mechanical stirrer, thermometer, and Dean-Stark water separator topped with a reflux condenser, was charged with 68.5 g (200 mmol) of sucrose, 52.3 g (210 mmol) of dibutyltin oxide, 400 ml of DMF, and 200 ml of benzene. The suspension was heated to reflux (106° C. reaction temperature), and the resulting clear solution refluxed for 2 hr.

The mixture was cooled to about 5° C., treated dropwise with 22.5 g (220 mmol) of acetic anhydride in 50 ml of ice-cold DMF, and stirred an additional 30 min at about 5° C. After stirring for 3.5 days at room temperature under argon, the reaction mixture was treated with 50 ml of H₂O, extracted with 1000 ml of cyclohexane to remove tin by-products, and the DMF evaporated (rotary evaporator, mechanical-pump vacuum, 30° C. water bath) to afford a light-tan viscous oil shown by HPLC analysis to contain 64.5 g (168 mmol, 83.9% yield) of sucrose-6-acetate.

EXAMPLE 5

PREPARATION OF SUCROSE-6-ACETATE USING DIBUTYLTIN OXIDE, DIMETHYLFORMAMIDE, AND HEXANE

A 1000-ml, three-neck, round-bottom flask, equipped with mechanical stirrer, thermometer, and Dean-Stark water separator topped with a reflux condenser, was charged with 68.5 g (200 mmol) of sucrose, 52 3 g (210 mmol) of dibutyltin oxide, 400 ml of DMF, and 100 ml of n-hexane The suspension was heated to reflux (77° C. reaction temperature), and held at this temperature for 24 hr.

The mixture was cooled to about 5° C., treated dropwise with 22.5 g (220 mmol) of acetic anhydride in 50 ml of ice-cold DMF, and stirred an additional 60 min at about 5° C. After stirring for 90 min at ambient temperature under argon, the reaction mixture was filtered (gravity, fluted paper), treated with H₂O (50 ml), extracted with cyclohexane (1 ×1000 ml), and the DMF evaporated (rotary evaporator, mechanical-pump vacuum, 30° C. water bath) to afford a brownish viscous oil determined by HPLC analysis to contain 58.7 g (153 mmol, 76.4% yield) of sucrose-6-acetate.

EXAMPLE 6

PREPARATION OF SUCROSE-6-ACETATE USING DIBUTYLTIN OXIDE, DIMETHYLFORMAMIDE, AND HEPTANE

A 1000-ml, three-neck, round-bottom flask, equipped with mechanical stirrer, thermometer, and Dean-Stark water separator topped with a reflux condenser, was charged with 68.5 g (200 mmol) of sucrose, 52.3 g (210 mmol) of dibutyltin oxide, 400 ml of DMF, and 200 ml of n-heptane The suspension was heated to reflux (98° C. reaction temperature), and the resulting clear solution refluxed for 3 hr. The contents of the water separator were removed, dissolved in anhydrous isopropanol, and analyzed (Karl Fischer) for water (3.81 g, 212 mmol, 101% of theory). The solution was cooled to about 5° C., treated dropwise with 22 5 g (220 mmol) of acetic anhydride dissolved in 50 ml of ice-cold DMF, and stirred for a further 60 min at about 5° C. After stirring overnight at room temperature under argon, the reaction mixture was treated with water (50 ml), extracted with cyclohexane (1 ×1000 ml) to remove tin-based by-products, and the DMF evaporated (rotary evaporator, mechanical-pump vacuum, 30° C. water bath) to afford a pale-yellow viscous oil determined by HPLC analysis to contain 65.5 g (171 mmol, 85.3% yield) of sucrose-6-acetate.

EXAMPLE 7

PREPARATION OF SUCROSE-6-BENZOATE USING DIBUTYLTIN OXIDE, DIMETHYLFORMAMIDE, AND HEPTANE

A 1000-ml, three-neck, round-bottom flask, equipped with mechanical stirrer, thermometer, and Dean-Stark water separator topped with a reflux condenser, was charged with 68.5 g (200 mmol) of sucrose, 52.3 g (210 mmol) of dibutyltin oxide, 400 ml of DMF, and 200 ml of n-heptane. The suspension was heated to reflux (98° C. reaction temperature), and the resulting clear solution refluxed for 3 hr. The contents of the water separator were removed, dissolved in anhydrous isopropanol, and subjected to Karl Fischer analysis for water (3.93 g, 218 mmol, 104% theory).

The solution was cooled in an ice bath, treated dropwise with 49 8 g (220 mmol) of benzoic anhydride dissolved in 50 ml of ice-cold DMF, and stirred for an additional 2 hr at ice-bath temperatures. After stirring overnight at room temperature under argon, the reaction mixture was treated with water (50 ml), extracted with cyclohexane (1 ×1000 ml), and the DMF evaporated (rotary evaporator, mechanical- pump vacuum, 30° C. water bath) to afford a light-yellow viscous oil determined by HPLC analysis to contain 85.6 g (192 mmol, 95.9% yield) of sucrose-6-benzoate. The oil was shown by AA spectrophotometry to contain 0.1% tin.

EXAMPLE 8

PREPARATION OF SUCROSE-6-ACETATE USING DIBUTYLTIN OXIDE, DIMETHYLFORMAMIDE, AND METHYL ETHYL KETONE

A 1000-ml, three-neck, round-bottom flask, equipped with mechanical stirrer, thermometer, and Dean-Stark water separator topped with a reflux condenser, was charged with 68.5 g (200 mmol) of sucrose, 52.3 g (210 mmol) of dibutyltin oxide, 400 ml of DMF, and 200 ml of methyl ethyl ketone. The suspension was heated to reflux (110° C. reaction temperature), and the resulting clear solution refluxed for 3 hr.

A separate water layer did not form in the water separator. After 1 hr and 2 hr of reflux time, the contents of the water separator were removed and enough methyl ethyl ketone (about 25 ml) was concomitantly added to the reaction medium to maintain a 108°-112° C. temperature. The 3-hr reflux-time water separator contents were removed and combined with the earlier two samples. Karl Fischer determination found 3.30 g (183 mmol, 87.3% of theory) of water.

The solution was cooled in an ice bath, treated dropwise with 22.5 g (220 mmol) of acetic anhydride dissolved in 50 ml of ice-cold DMF, and stirred for an additional 30 min at ice-bath temperatures. After stirring overnight at room temperature under argon, the reaction mixture was subjected to rotary evaporation (water-aspirator vacuum, 60° C. bath temperature) to remove the methyl ethyl ketone, treated with 100 ml of DMF and 50 ml of water, and extracted with cyclohexane (1×1000 ml) to remove organotin by-products. Evaporation of the DMF (rotary evaporator, mechanical-pump vacuum, 30° C. water bath) afforded a dark viscous oil determined by HPLC analysis to contain 56.2 g (146 mmol, 73.1% yield) of sucrose-6-acetate and 4.68 g (13.7 mmol, 6.84% recovery) of sucrose.

EXAMPLE 9

PREPARATION OF SUCROSE-6-ACETATE USING DIBUTYLTIN OXIDE, DIMETHYLFORMAMIDE, AND ISOOCTANE

A 1000-ml, three-neck, round-bottom flask, equipped with mechanical stirrer, thermometer, and Dean-Stark water separator topped with a reflux condenser, was charged with 68.5 g (200 mmol) of sucrose, 52.3 g (210 mmol) of dibutyltin oxide, 400 ml of DMF, and 200 ml of isooctane. The suspension was heated to reflux (100° C. reaction temperature), and the resulting clear solution refluxed for 3 hr. The contents of the water separator were removed, dissolved in anhydrous isopropanol, and subjected to Karl Fischer water analysis (4.20 g, 233 mmol, 111% of theory).

The solution was cooled in an ice bath, treated dropwise with 22.5 g (220 mmol) of acetic anhydride dissolved in 50 ml of ice-cold DMF, and stirred for an additional 60 min under argon at ice-bath temperatures. The TLC system described in Example 1 indicated that the conversion was complete at this time.

The reaction mixture was treated with 50 ml of H$_2$O, extracted with 1000 ml of cyclohexane, and the DMF removed (rotary evaporator, mechanical-pump vacuum, 30° C. water bath) to give a pale-yellow viscous oil shown by HPLC analysis to contain 60.6 g (158 mmol, 78.8% yield) of sucrose-6-acetate.

EXAMPLE 10

PREPARATION OF SUCROSE-6-ACETATE USING DIBUTYLTIN OXIDE, DIMETHYLFORMAMIDE, AND CYCLOHEXANE

A 2000-ml, three-neck, round-bottom flask, equipped with mechanical stirrer, thermometer, and Dean-Stark water separator topped with a reflux condenser, was charged with 200 g (0.584 mol) of sucrose, 153 g (0.613 mol) of dibutyltin oxide, 700 ml of DMF, and 200 ml of cyclohexane. The suspension was heated to reflux (88° C. reaction temperature), and the resulting clear solution refluxed for 5 hr. The water separator was drained as required with the concurrent addition of 25-ml portions of cyclohexane to the reaction mixture in order to maintain a 92°-3° C. temperature. The combined contents of the water separator were dissolved in anhydrous isopropanol and subjected to Karl Fischer water analysis (12.2 g, 0.676 mol, 110% of theory).

The solution was cooled to about 5° C., treated dropwise over 10 min with 65.6 g (0.643 mol) of acetic anhydride (maximum temperature 10° C.), and stirred for an additional 60 min at 5°-10° C. under argon. The reaction appeared to be complete after this time using the TLC system described in Example 1.

The reaction mixture was treated with 50 ml of H$_2$O and extracted with cyclohexane (500 ml). The layers were separated and the cyclohexane layer discarded. The DMF layer was then treated with an additional 50 ml of H$_2$O and 250 ml of DMF, and further extracted with cyclohexane (3×500 ml). The cyclohexane layers were discarded, and the DMF layer evaporated (rotary evaporator, mechanical-pump vacuum, 30° C. water bath) to give a pale-yellow viscous oil shown by HpLC analysis to contain 198 g (0.517 mol, 88.4% yield) of sucrose-6-acetate. The oil was determined by AA spectrophotometry to contain 0.08% tin.

EXAMPLE 11

PREPARATION OF SUCROSE-6-ACETATE USING DIBUTYLTIN OXIDE, N-METHYL-2-PYRROLIDONE, AND CYCLOHEXANE

A 1000-ml, three-neck, round-bottom flask, equipped with mechanical stirrer, thermometer, Dean-Stark water separator topped with a reflux condenser, was charged with 68.5 g (200 mmol) of sucrose, 52.3 g (210 mmol) of dibutyltin oxide, 400 ml of N-methyl-2-pyrrolidone, and 200 ml of cyclohexane. The mixture was refluxed for 5.5 hr (90° C. reaction temperature). The suspension became homogeneous after about 4 hr. The contents of the water separator were dissolved in anhydrous isopropanol and analyzed for water by the Karl Fischer method (3.63 g, 201 mmol, 95.9% of theory).

The solution was cooled to about 5° C., treated dropwise over 15 min with 22.5 g (220 mmol) of acetic anhydride dissolved in 50 ml of ice-cold DMF, and stirred for an additional 30 min at 3°–5° C. After stirring overnight at room temperature under argon, the reaction mixture was treated with $H_2O$ (50 ml), extracted with cyclohexane (2 ×500 ml), and the methylpyrrolidone layer evaporated (rotary evaporator, mechanical-pump vacuum, 45° C. water bath) to give a brownish viscous oil determined by HPLC analysis to contain 64.1 g (167 mmol, 83.4% yield) of sucrose-6-acetate. The oil was shown by AA spectrophotometry to contain 0.1 wt % tin.

EXAMPLE 12

PREPARATION OF SOLID SUCROSE-6-BENZOATE USING DIBUTYLTIN OXIDE, DIMETHYLFORMAMIDE, AND BENZENE

A 1000-ml, three-neck, round-bottom flask, equipped with mechanical stirrer, thermometer, Dean-Stark water separator topped with a reflux condenser, was charged with 68.5 g (200 mmol) of sucrose, 52.3 g (210 mmol) of dibutyltin oxide, 400 ml of DMF, and 200 ml of benzene. The suspension was heated to reflux (107° C. reaction temperature), and the resulting clear solution refluxed for 2 hr. The contents of the water separator were dissolved in anhydrous isopropanol and analyzed for water by the Karl Fischer method (3.66 g, 203 mmol, 96.9% of theory).

The solution was cooled in an ice bath, treated dropwise over 30 min with 49.8 g (220 mmol) of benzoic anhydride dissolved in 50 ml of ice-cold DMF, and then stirred for an additional 30 min at ice-bath temperatures. After stirring overnight at room temperature under argon, the two solvents were removed by rotary evaporation (water-aspirator vacuum, 50° C. bath followed by mechanical-pump vacuum, 30° C. bath) to afford a viscous oil which was treated in the rotary evaporator with 250 ml of acetone. Heating to about 50° C. produced a clear solution from which sucrose-6-benzoate readily crystallized on cooling to room temperature.

The product was filtered on a coarse-frit, sintered-glass filter, washed with acetone (2×100 ml), and vacuum dried (50° C./0.5 mm of Hg/16 hr) to produce 70.0 g of off-white solid shown by HPLC analysis to consist of 98.1% sucrose-6-benzoate (68.7 g, 154 mmol, 76.9% yield). The solid was shown by AA spectrophotometry to contain 0.43% tin.

EXAMPLE 13

PREPARATION OF SUCROSE-6-ACETATE USING DIBUTYLTIN OXIDE, DIMETHYLFORMAMIDE, AND CHLOROFORM

A 1000-ml, three-neck, round-bottom flask, equipped with mechanical stirrer, thermometer, and Kontes Glassware heavier-than-water water-solvent separator (catalog #535800-0000) topped with a reflux condenser, was charged with 68.5 g (200 mmol) of sucrose, 52.3 g (210 mmol) of dibutyltin oxide, 400 ml of DMF, and 250 ml of chloroform. The suspension was heated to reflux (103° C. reaction temperature, 87° C. water-separator vapor temperature), and the resulting clear solution refluxed for 3 hr.

At ambient temperature, the solution was treated in one portion with 22.5 g (220 mmol) of acetic anhydride. A slow exotherm raised the reaction temperature from 23° C. to 30° C. over about 15 min. After stirring overnight at room temperature under argon, the reaction mixture was treated with $H_2O$ (50 ml), extracted with cyclohexane (2×1000 ml) to remove tin by-products, and the DMF layer evaporated to afford a blackish-brown viscous oil shown by HPLC analysis to contain 56.0 g (146 mmol, 72.9% yield) of sucrose-6-acetate. This oil was determined by AA spectrophotometry to contain 0.1% tin.

EXAMPLE 14

PREPARATION OF SOLID SUCROSE-6-BENZOATE USING DIBUTYLTIN OXIDE, DIMETHYLFORMAMIDE, AND HEPTANE

A 1000-ml, three-neck, round-bottom flask, equipped with mechanical stirrer, thermometer, and Dean-Stark water separator topped with a reflux condenser, was charged with 68.5 g (200 mmol) of sucrose, 52.3 g (210 mmol) of dibutyltin oxide, 400 ml of DMF, and 200 ml of n-heptane. The suspension was heated to reflux (98° C. reaction temperature), and the resulting clear solution refluxed for 3 hr. The contents of the water separator were dissolved in anhydrous isopropanol and analyzed for water by the Karl Fischer method (3.39 g, 188 mmol, 89.8% of theory).

The solution was treated in one portion at room temperature with 49.8 g (220 mmol) of benzoic anhydride dissolved in 50 ml of DMF. A slow exotherm raised the reaction temperature from 26° C. to 30° C. over about 20 min. After stirring overnight at room temperature under argon, the two solvents were removed by rotary evaporation (water-aspirator vacuum, 40° C. bath followed by mechanical-pump vacuum, 30° C. bath) to afford a viscous oil which was treated on the rotary evaporator with 250 ml of acetone. Heating this mixture to about 50° C. produced a clear solution from which sucrose-6-benzoate readily crystallized on cooling to room temperature.

The product was filtered on a coarse-frit, sintered-glass filter, washed with acetone (2×100 ml), and vacuum dried (50° C./0.5 mm of Hg/14 hr) to produce 69.3 g of white solid shown by HPLC analysis to consist of 97.0% sucrose-6-benzoate (67.2 g, 151 mmol, 75.3% yield). The solid was determined by AA spectrophotometry to contain 0.40% tin.

EXAMPLE 15

PREPARATION OF SOLID SUCROSEDIBUTYLTIN-6ACETATE USING OXIDE, DIMETHYLFORMAMIDE, AND CYCLOHEXANE

A 2000-ml, four-neck, round-bottom flask, equipped with mechanical stirrer, thermometer, dropping funnel, and Dean-Stark water separator topped with a reflux condenser, was charged with 200 g (0.584 mol) of sucrose, 153 g (0.613 mol) of dibutyltin oxide, 700 ml of DMF, and 100 ml of cyclohexane. The suspension was heated to reflux (100° C. reaction temperature), and the resulting clear solution refluxed for 5 hr. The lower layer of the water separator was removed as necessary with the concurrent addition of cyclohexane (25 ml total) in order to maintain a 100±1° C. temperature. The combined contents of the water separator were analyzed for water by the Karl Fischer method (11.7 g, 0.651 mol, 106% of theory).

The mixture was cooled to about −4° C. using a dry ice-acetone bath, treated dropwise over 40 min with 64.4 g (0.631 mol) of acetic anhydride (maximum temperature −1° C.), and stirred for an additional 20 min at about −2° C. The reaction appeared to be complete after this time using the TLC system described in Example 1.

After stirring overnight at room temperature, the reaction mixture was treated with 20 ml of H₂O and extracted with cyclohexane (1×500 ml followed by 1×250 ml). The cyclohexane layers were discarded. The DMF layer was then treated with an additional 20 ml of H₂O, and further extracted with cyclohexane (2×250 ml). The cyclohexane layers were discarded, and the DMF layer evaporated (rotary evaporator, mechanical-pump vacuum, 30° C. water bath) to give a dark-tan viscous oil shown by HPLC analysis to contain 197 g (0.513 mol, 87.9% yield) of sucrose-6-acetate. The oil was determined by AA spectrophotometry to contain 0.1% tin.

The syrup prepared above was combined with a similar sample containing 101 g (0.263 mol) of sucrose-6-acetate, and as much residual DMF removed as possible (rotary evaporator, mechanical-pump vacuum, 50° C. water bath). The residue was dissolved in hot methanol (300 ml), cooled to about 5° C., seeded with sucrose-6-acetate crystals, allowed to stand at 5° C. overnight, and filtered using a coarse-frit sintered-glass filter. The filter cake was reslurried in 200 ml of methanol, filtered, and the filter cake washed with 100 ml of methanol. After vacuum drying (25° C./0.5 mm of Hg/18 hr), there was obtained 246 g of off-white solid shown by HPLC analysis to consist of 82.4% sucrose-6-acetate (203 g, 0.528 mol, 68.0% recovery), 1.3% sucrose, and 2.5% sucrose diacetates. Gas chromatographic and Karl Fischer analyses showed that the solid also contained significant amounts of methanol (5.8%), DMF (3.3%), and water (1.1%).

A 100-g sample of the crude solid (82.4 g, 0.215 mol, of S-6-A) was treated with 5 g of activated carbon in 550 ml of methanol at reflux for 10 min. The carbon was removed by filtration and the carbon cake washed with 150 ml of hot methanol. The filtrate and washings were combined, concentrated to about 500 ml volume, cooled to about 10° C., and seeded. The product was filtered, immediately redissolved in 550 ml of refluxing methanol, concentrated to about 500 ml volume, cooled to about 10° C., and let stand overnight. The white solid thus obtained was filtered, washed with cold methanol (100 ml), and vacuum dried (50° C./0.5 mm of Hg/16 hr) to afford a product (74.4 g) determined by a combination of analyses to consist of 90.2% sucrose-6-acetate (67.1 g, 0.175 mol, 81.3% recovery basis crude solid and 55.3% recovery basis extracted DMF syrup), 0.6% sucrose, 1.7% sucrose diacetates, 6.8% methanol, and 0.2% water. It was found that the methanol content of solid sucrose-6-acetate prepared in this manner cannot be decreased by extended vacuum drying.

EXAMPLE 16

PREPARATION OF SOLID SUCROSE-6-BENZOATE USING DIBUTYLTIN OXIDE, DIMETHYLFORMAMIDE, AND TOLUENE

A 2000-ml, one-neck, round-bottom flask, equipped with magnetic stirrer and Dean-Stark water separator topped with a reflux condenser, was charged with 100 g (292 mmol) of sucrose and 400 ml of DMF. This mixture was heated and stirred at 90° C. (bath) until homogeneous (approximately 10 min).

The solution was treated with 73.6 g (296 mmol) of dibutyltin oxide and 50 ml of toluene, and the suspension thus produced heated at 110° C. (bath) for 1.5 hr followed by additional heating at 125° C. (bath) for 1.5 hr. During this heating period a slight vacuum was applied to the system in order to produce reflux. The contents of the water separator were drained as necessary with the concurrent addition of toluene (30 ml total) to insure adequate reflux.

The dark solution thus obtained was cooled to room temperature and treated in one portion with 69.4 g (307 mmol) of benzoic anhydride. After stirring at room temperature overnight, the solvents were removed by rotary evaporation (mechanical-pump vacuum, 50° C. water bath) to afford a syrup which was treated on the rotary evaporator with 500 ml of acetone. Heating to about 50° C. produced a solution from which sucrose-6-benzoate was induced to crystallize on cooling to room temperature by seeding.

The slurry was diluted with 250 ml of acetone, stirred for 2 hr at 0°–5° C., and filtered on a coarse-frit sintered-glass filter. The product was twice reslurried in 100 ml of acetone, refiltered, and the filter cake washed with 50 ml of acetone. Vacuum drying (25° C./0.5 mm of Hg/14 hr) afforded 103 g of white solid determined by HPLC analysis to consist of 92.3% sucrose-6-benzoate (95.0 g, 213 mmol, 72.9% yield).

EXAMPLE 17

PREPARATION OF SUCROSE-6-BENZOATE USING DIBUTYLTIN OXIDE, DIMETHYLFORMAMIDE, AND TETRAHYDROFURAN

A 1000-ml, three-neck, round-bottom flask, equipped with mechanical stirrer, thermometer, 125-ml nonpressure-equalizing dropping funnel, and Kontes Glassware water-solvent separator (catalog #535800-0000) topped with a reflux condenser, was charged with 68.5 g (200 mmol) of sucrose, 52.3 g (210 mmol) of dibutyltin oxide, 400 ml of DMF, and 200 ml of tetrahydrofuran (THF).

The suspension was heated to reflux, and the resulting clear solution refluxed for 7.5 hr.

A separate water layer did not form in the water separator. At approximately 30-min intervals, the contents of the water separator were drained and enough THF (375 ml total) concurrently added to maintain a 100±2° C. reaction temperature and an 82±3° C. water-separator vapor temperature. The combined contents of the water separator were analyzed by the Karl Fischer method (3.54 g, 197 mmol, 93.7% of theory).

The solution was treated at room temperature over 20 min with 49.8 g (220 mmol) of benzoic anhydride dissolved in 50 ml of DMF. A slow exotherm raised the reaction temperature from 19° C. to 25° C. After stirring overnight at room temperature under argon, the reaction mixture was treated with water (50 ml), extracted with cyclohexane (1 ×1000 ml), and the DMF evaporated (rotary evaporator, mechanical-pump vacuum, 30° C. water bath) to afford a dark-brown viscous oil determined by HPLC analysis to contain 69.9 g (157 mmol, 78.4% yield) of sucrose-6-benzoate.

EXAMPLE 18

PREPARATION OF SUCROSE-6-ACETATE USING DIBUTYLTIN OXIDE, DIMETHYLFORMAMIDE, AND CYLCOHEXANE WITH DEMONSTRATION OF DIBUTYLTIN OXIDE RECYCLE

Sucrose (100 g, 292 mmol) was treated with 76.3 g (307 mmol) of dibutyltin oxide and converted to sucrose-6-acetate (84.4 g, 220 mmol, 75.3% yield) essentially as described in Example 10, except that the combined and evaporated cyclohexane extracts which contained 1,3-diacetyl-1,1,3,3-tetrabutyldistannoxane or distannoxane diacetate ("DSDA") were added at 60° C. to 13.0 g (325 mmol) of sodium hydroxide in 250 ml of water. After removal of residual cyclohexane by atmospheric pressure distillation, the slurry thus produced was cooled to 30° C., filtered (basket centrifuge), and the recovered dibutyltin oxide ("DBTO") washed with water (3×100 ml). The wet weight of recovered solid was 81.8 g.

The recovered DBTO was employed to produce a second batch of sucrose-6-acetate, and the DBTO recovered yet again. A third batch of sucrose-6-acetate was then prepared with the twice-recovered DBTO. Complete data for this set of three sequential reactions is presented below.

|  | Original | First Recycle | Second Recycle |
|---|---|---|---|
| Sucrose (g) | 100 | 100 | 100 |
| Sucrose (mmol) | 292 | 292 | 292 |
| Sucrose (equiv) | 1.00 | 1.00 | 1.00 |
| Recycle DBTO (g) | — | 75.1* | 74.8* |
| Recycle DBTO (mmol) | — | 302 | 301* |
| Fresh DBTO (g) | 76.3 | 1.20 | 1.50 |
| Fresh DBTO (mmol) | 307 | 4.82 | 6.03 |
| Total DBTO (mmol) | 307 | 307 | 307 |
| Total DBTO (equiv) | 1.05 | 1.05 | 1.05 |
| DMF (ml) | 400 | 350 | 350 |
| Cyclohexane (ml) | 75 | 75 | 65 |
| Anhydride (g) | 39.6 | 36.4 | 34.4 |
| Anhydride (mmol) | 387 | 357 | 337 |
| Anhydride (equiv) | 1.33 | 1.22 | 1.15 |
| S-6-A (g) | 84.4 | 88.2 | 90.5 |
| S-6-A (mmol) | 220 | 230 | 236 |
| S-6-A (equiv) | 75.3 | 78.7 | 80.7 |

*dry basis

The following table displays the experimental details and yields for Examples 1-17:

| | | | | SUCROSE-6-ESTER PRODUCTION | | | | | | | |
|---|---|---|---|---|---|---|---|---|---|---|---|
| EXAMP | ALKYL[1] | SOLV | COSOLV | TEMP[2] | TIME[3] | Water[4] | ESTER[5] | TEMP[6] | TIME[7] | ISOL[8] | YIELD[9] |
| 1 | octyl | DMF | heptane | 98 | 3 | 107 | B | 5/25 | 1.0/16 | NO | 90.1 |
| 2 | octyl | DMF | isooctane | 101 | 3 | 106 | A | 5/25 | 3.0/16 | NO | 78.5 |
| 3 | butyl | DMF | cyclohex | 93 | 4 | 105 | B | 5/25 | 0.5/16 | NO | 94.4 |
| 4 | butyl | DMF | benzene | 106 | 2 | NA | A | 5/25 | 0.5/84 | NO | 83.9 |
| 5 | butyl | DMF | hexane | 77 | 24 | NA | A | 5/25 | 1.0/1.5 | NO | 76.4 |
| 6 | butyl | DMF | heptane | 98 | 3 | 101 | A | 5/25 | 1.0/16 | NO | 85.3 |
| 7 | butyl | DMF | heptane | 98 | 3 | 104 | B | 5/25 | 2.0/16 | NO | 95.9 |
| 8 | butyl | DMF | MEK | 110 | 3 | 87 | A | 5/25 | 0.5/16 | NO | 73.1 |
| 9 | butyl | DMF | isooctane | 100 | 3 | 111 | A | 5/— | 1.0/— | NO | 78.8 |
| 10 | butyl | DMF | cyclohex | 92 | 5 | 110 | A | 5/— | 1.0/— | NO | 88.4 |
| 11 | butyl | NMP | cyclohex | 90 | 5.5 | 96 | A | 5/25 | 0.5/16 | NO | 83.4 |
| 12 | butyl | DMF | benzene | 107 | 2 | 97 | B | 5/25 | 0.5/16 | YES | 76.9 |
| 13 | butyl | DMF | CHCl$_3$ | 103 | 3 | NA | A | 25 | 16 | NO | 72.9 |
| 14 | butyl | DMF | heptane | 98 | 3 | 90 | B | 25 | 16 | YES | 75.3 |
| 15 | butyl | DMF | cyclohex | 100 | 5 | 106 | A | −2/25 | 1.0/16 | YES | 87.9[10] |
| 16 | butyl | DMF | toluene | NA | 3 | NA | B | 25 | 16 | YES | 72.9 |
| 17 | butyl | DMF | THF | 100 | 7.5 | 94 | B | 25 | 16 | NO | 78.4 |

Footnotes for Table
[1]Tin-bound alkyl group.
[2]Reaction temp in °C. for sucrose-dialkyltin adduct formation.
[3]Reaction time in hr for sucrose-dialkyltin adduct formation.
[4]Percent of theory H$_2$O (basis one H$_2$O per DBTO unit) produced during sucrose-dialkyltin adduct formation (Karl Fischer method).
[5]Sucrose-6-ester prepared. B is benzoate, and A is acetate.
[6]Temperature in °C. employed for the acylation step.
[7]Time in hr employed for the acylation step.
[8]A "yes" in this column means the product was isolated as a purified solid.
[9]Percent yield based upon HPLC determination.
[10]This yield is for product in the purified syrup.

What is claimed is:

1. Process which consists essentially of reacting sucrose with a di(hydrocarbyl)tin oxide in an inert organic reaction vehicle with removal of water for a period of time and at a temperature sufficient to produce a 1,3-di-(6-O-sucrose)-1,1,3,3-tetra(hydrocarbyl)distannoxane.

2. The process of claim 1 wherein the di(hydrocarbyl)tin oxide is a dialkyltin oxide.

3. The process of claim 2 wherein the dialkyltin oxide is dibutyltin oxide or dioctyltin oxide.

4. The process of claim 1 wherein the inert organic reaction vehicle is a mixture of a polar aprotic solvent and an organic liquid (1) that produces a mixture with the polar aprotic solvent, the di(hydrocarbyl)tin oxide, and the sucrose which refluxes with an internal reaction temperature within the range of from about 75° C. to about 125° C., (2) that is capable of codistilling the water produced by the condensation of the di(hydrocarbyl)tin oxide and sucrose, and (3) that promotes the solubility of the di(hydrocarbyl)tin oxide.

5. The process of claim 2 wherein the inert organic reaction vehicle is a mixture of a polar aprotic solvent and an organic liquid (1) that produces a mixture with the polar aprotic solvent, the di(hydrocarbyl)tin oxide, and the sucrose which refluxes with an internal reaction temperature within the range of from about 75° C. to about 125° C., (2) that is capable of codistilling the water produced by the condensation of the di(hydrocarbyl)tin oxide and sucrose, and (3) that promotes the solubility of the di(hydrocarbyl)tin oxide.

6. The process of claim 3 wherein the inert organic reaction vehicle is a mixture of a polar aprotic solvent and an organic liquid (1) that produces a mixture with the polar aprotic solvent, the di(hydrocarbyl)tin oxide, and the sucrose which refluxes with an internal reaction temperature within the range of from about 75° C. to about 125° C., (2) that is capable of codistilling the water produced by the condensation of the di(hydrocarbyl)tin oxide and sucrose, and (3) that promotes the solubility of the di(hydrocarbyl)tin oxide.

7. The process of claim 4 wherein the polar aprotic solvent is N,N-dimethylformamide or N-methylpyrrolidone and the said organic liquid is a chlorinated hydrocarbon, a saturated hydrocarbon, an aromatic hydrocarbon, a ketone, or an ether.

8. The process of claim 5 wherein the polar aprotic solvent is N,N-dimethylformamide or N-methylpyrrolidone and the said organic liquid is a chlorinated hydrocarbon, a saturated hydrocarbon, an aromatic hydrocarbon, a ketone, or an ether.

9. The process of claim 6 wherein the polar aprotic solvent is N,N-dimethylformamide or N-methylpyrrolidone and the said organic liquid is a chlorinated hydrocarbon, a saturated hydrocarbon, an aromatic hydrocarbon, a ketone, or an ether.

10. The process of claim 7 wherein the said organic liquid is a member selected from the group consisting of hexane, heptane, octane, cyclohexane, benzene, toluene, chloroform, methyl ethyl ketone, and tetrahydrofuran.

11. The process of claim 8 wherein the said organic liquid is a member selected from the group consisting of hexane, heptane, octane, cyclohexane, benzene, toluene, chloroform, methyl ethyl ketone, and tetrahydrofuran.

12. The process of claim 9 wherein the said organic liquid is a member selected from the group consisting of hexane, heptane, oxtane, cyclohexane, benzene, toluene, chloroform, methyl ethyl ketone, and tetrahydrofuran.

13. The process for producing a sucrose-6-ester which consists essentially of reacting sucrose with a di(hydrocarbyl)tin oxide in an inert organic reaction vehicle with removal of water for a period of time and at a temperature sufficient to produce a 1,3-di-(6-O-sucrose)-1,1,3,3-tetra(hydrocarbyl)distannoxane which is subjected to a further step of reaction with an acylating agent at a temperature and for a period of time sufficient to produce the sucrose-6-ester.

14. The process of claim 13 wherein the acylating agent is a carboxylic acid anhydride.

15. The process of claim 14 wherein the carboxylic acid anhydride is acetic anhydride or benzoic anhydride.

* * * * *

UNITED STATES PATENT AND TRADEMARK OFFICE
CERTIFICATE OF CORRECTION

PATENT NO. : 5,023,329
DATED : June 11, 1991
INVENTOR(S) : David S. Neiditch et al.

It is certified that error appears in the above-identified patent and that said Letters Patent is hereby corrected as shown below:

Column 22, Line 21, Claim 12 - "oxtane" should be -- octane --.

Signed and Sealed this

Twenty-second Day of December, 1992

*Attest:*

DOUGLAS B. COMER

*Attesting Officer*   *Acting Commissioner of Patents and Trademarks*